United States Patent
Al-Ali et al.

(10) Patent No.: US 6,542,764 B1
(45) Date of Patent: Apr. 1, 2003

(54) PULSE OXIMETER MONITOR FOR EXPRESSING THE URGENCY OF THE PATIENT'S CONDITION

(75) Inventors: Ammar Al-Ali, Tustin, CA (US); Massi E. Kiani, Laguna Niguel, CA (US)

(73) Assignee: Masimo Corporation, Irvine, CA (US)

( * ) Notice: Subject to any disclaimer, the term of this patent is extended or adjusted under 35 U.S.C. 154(b) by 220 days.

(21) Appl. No.: 09/727,944

(22) Filed: Dec. 1, 2000

Related U.S. Application Data
(60) Provisional application No. 60/168,366, filed on Dec. 1, 1999.

(51) Int. Cl.[7] .................................................. A61B 5/00
(52) U.S. Cl. ...................................... 600/323; 600/479
(58) Field of Search ................................ 600/322–324, 600/310, 479, 502, 509, 514; 340/573.1; 356/39, 41

(56) References Cited

U.S. PATENT DOCUMENTS

| | | |
|---|---|---|
| 2,706,927 A | 4/1955 | Wood |
| 3,565,058 A | 2/1971 | Mansfield et al. |
| 3,638,640 A | 2/1972 | Shaw |

(List continued on next page.)

FOREIGN PATENT DOCUMENTS

| | | |
|---|---|---|
| DE | 23 50 409 A1 | 4/1975 |
| DE | 29 11 056 A1 | 9/1980 |
| EP | 0 262 779 A1 | 4/1988 |
| EP | 0 481 612 A1 | 4/1992 |
| EP | 0 745 348 A1 | 4/1996 |
| FR | 1.589.461 | 5/1970 |
| GB | 2 039 364 A | 6/1980 |
| JP | 50-88873 | 7/1975 |
| JP | 51-25391 | 3/1976 |
| JP | 53-53184 | 5/1978 |
| JP | 53-88778 | 8/1978 |
| JP | 54-54063 | 4/1979 |
| JP | 57-125990 | 8/1982 |
| JP | 1034149 | 2/1998 |
| WO | WO 82/01948 | 6/1982 |
| WO | WO 97/23159 | 7/1997 |

OTHER PUBLICATIONS

I. Yoshiya et al., "Principle and Performance of Novel Non–Invasive Arterial Blood Oxygen Saturation Measuring Apparatus (OXIMET)," Journal of Intensive Care Medicine, vol. 2, No. 6, pp. 455–460 (1978).

(List continued on next page.)

*Primary Examiner*—Joseph Pelham
(74) *Attorney, Agent, or Firm*—Knobbe, Martens, Olson & Bear, LLP

(57) ABSTRACT

A monitor for a pulse oximeter emits audible sounds containing information regarding the patient's pulse rate and oxygen saturation level wherein the information is not contained in variations of the pitch of the audible sounds. By utilizing sets of audible sounds pulsed in synchroneity with the heartbeat of the patient in which the sound volume is a function of the patient's oxygen saturation level, the urgency of the patient's condition is effectively expressed to the monitoring individual. Alternatively, the urgency of the patient's condition is effectively expressed by varying the number of audible sounds in each set of audible sounds, or by varying the volume shape of each audible sound. The present invention represents an improvement over the monitors described in the prior art which utilize variations of pitch with oxygen saturation level because the present invention requires less training and less subjective judgment, can be more quickly interpreted, and is less affected by hearing disabilities of the monitoring individuals.

17 Claims, 4 Drawing Sheets

U.S. PATENT DOCUMENTS

| | | | |
|---|---|---|---|
| 3,658,060 A | | 4/1972 | Eklof |
| 3,704,706 A | | 12/1972 | Harczfeld et al. |
| 3,875,930 A | | 4/1975 | Silva et al. |
| 3,895,316 A | | 7/1975 | Fein |
| 3,998,550 A | | 12/1976 | Konishi et al. |
| 4,013,067 A | | 3/1977 | Kresse et al. |
| 4,038,976 A | | 8/1977 | Hardy et al. |
| 4,052,977 A | | 10/1977 | Kay |
| 4,109,643 A | | 8/1978 | Bond et al. |
| 4,159,018 A | | 6/1979 | Brastad |
| 4,167,331 A | | 9/1979 | Nielsen |
| 4,246,906 A | | 1/1981 | Winberg et al. |
| 4,266,554 A | | 5/1981 | Hamaguri |
| 4,424,814 A | | 1/1984 | Secunda |
| 4,685,464 A | | 8/1987 | Goldberger et al. |
| 4,759,369 A | * | 7/1988 | Taylor ..................... 128/633 |
| 4,653,498 A | | 4/1989 | New, Jr. et al. |
| 4,869,253 A | * | 9/1989 | Craig, Jr. et al. ........... 128/633 |
| RE33,643 E | | 7/1991 | Isaacson et al. |
| 5,190,038 A | * | 3/1993 | Polson et al. ............... 128/633 |
| 5,247,931 A | | 9/1993 | Norwood |
| 5,309,908 A | | 5/1994 | Friedman et al. |
| 5,313,940 A | | 5/1994 | Fuse et al. |
| 5,438,986 A | | 8/1995 | Disch et al. |
| 5,588,427 A | | 12/1996 | Tien |
| 5,632,272 A | | 5/1997 | Diab et al. |
| 5,730,140 A | | 3/1998 | Fitch |
| 2002/0095077 A1 | * | 7/2002 | Swedlow et al. ........... 600/323 |

OTHER PUBLICATIONS

K. Ikeda et al., "*Method for Display of Biological Information: Application to Display of Blood Pressure,*" Japanese Journal of Medical Electronics and Biological Engineering, vol. 15, special issue, pp. 382–383 (1977). (Certified Translation Attached).

PCT International Search Report, App. No.: PCT/US00/22849, App. Date: Aug. 21, 2000, 4 pages.

Leoeb, M.D., Robert G. "Laboratory Evaluation of an Auditory Display Designed to Enhance Intra–Operative Monitoring," *http:///www.gasnet.org/societies/sta/publications/Annual_2000/Loeb.html*, 2 pages downloaded and printed from the World Wide Web on Apr. 12, 2001.

* cited by examiner

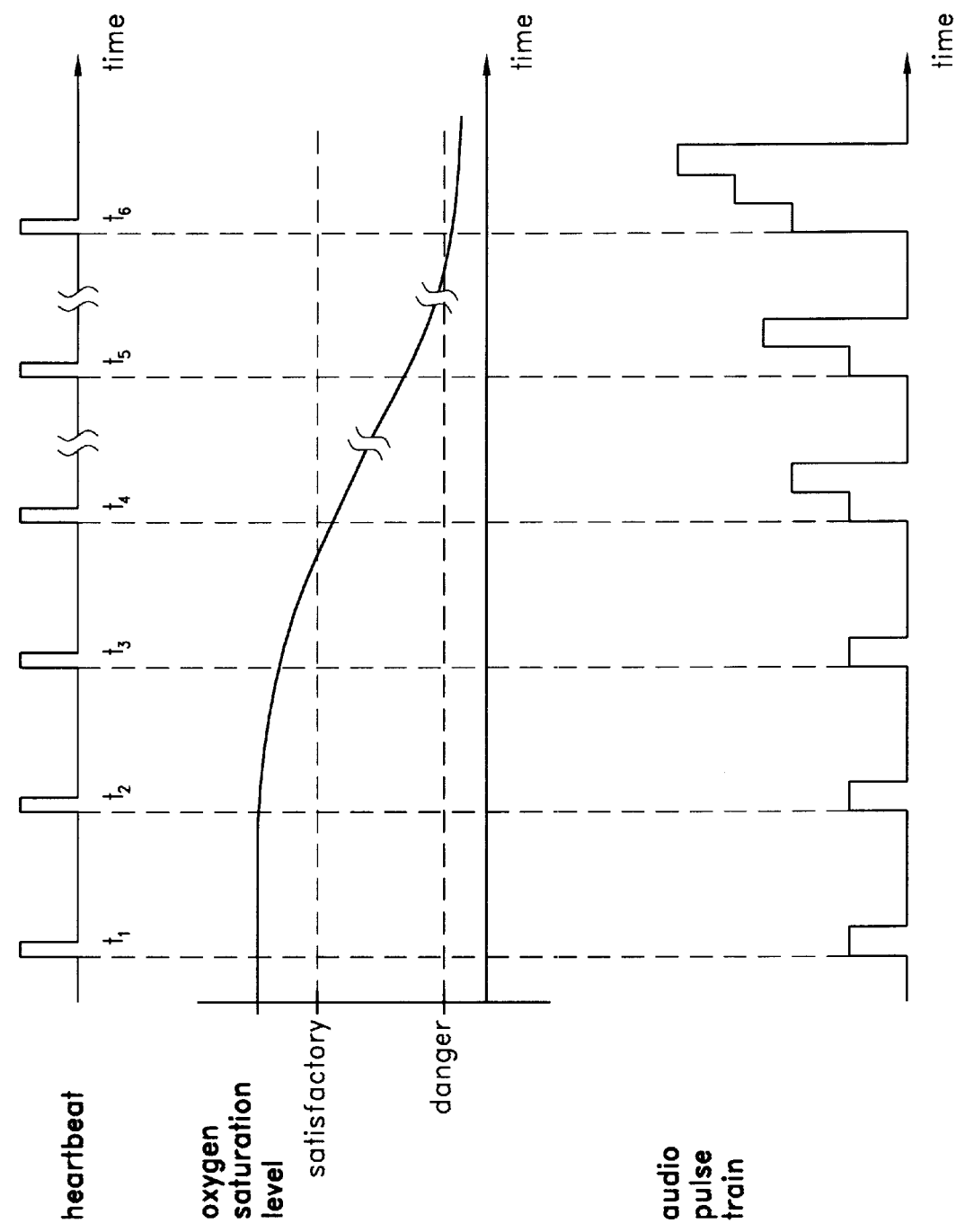

PULSE OXIMETER MONITOR FOR EXPRESSING THE URGENCY OF THE PATIENT'S CONDITION

Related Applications

This application claims the benefit of priority under 35 U.S.C. § 119(e) of U.S. Provisional Patent App. No. 60/168,366 filed on Dec. 1, 1999 and entitled Pulse Oximeter Monitor for Expressing the Urgency of the Patient's Condition.

BACKGROUND OF THE INVENTION

1. Field of the Invention

The invention relates to pulse oximeters and methods for expressing the urgency of the patient's condition to the monitoring individuals.

2. Description of the Related Art

Pulse oximeters measure the oxygen saturation in pulsatile arterial blood by analyzing the variations in light transmission through a section of body tissue, and are well-known in the art. As disclosed by Wood in U.S. Pat. No. 2,706,927, the oxygen saturation can be calculated from two measurements of light absorption at two different wavelengths by a section of body tissue. The quantity of arterial blood in a section of body tissue varies in synchroneity with the heartbeat, so heartbeat-synchronized variations in the transmitted light intensity therefore correspond to variations of the pulsatile arterial blood. Because the absorption coefficient of the oxyhemoglobin component of blood can be determined, a comparison of the transmitted light intensities at different moments during the periodic heartbeat can be converted into a measure of the fraction of oxyhemoglobin in arterial blood, i.e., the arterial oxygen saturation. Various methods of calculating the oxygen saturation level are known in the prior art, such as, for example, the methods disclosed in Diab et al., U.S. Pat. No. 5,632,272, issued May 27, 1997.

SUMMARY OF THE INVENTION

The present inventors recognized several disadvantages inherent in the pulse oximeter monitor technology described in the prior art. First, in order to be able to interpret the information contained in the variations of the pitch of the audible sounds created by the prior art devices, a health care individual such as a nurse must be able to put the audible sounds in the correct context. To audibly detect a problem, the individual must have some experience in discerning the difference between a sound pitch which is within tolerances and a sound pitch which is indicative of a problem. Using sound pitch as the measure of oxygen saturation therefore requires cognitive thought by the individual who has been trained to recognize the sound pitches associated with low oxygen saturation conditions. Such high-level thought processes occur more slowly, and are more prone to mistakes in judgment, than are other, more instinctive, thought processes. Second, the monitors described in the prior art which use sound pitch as an indication of low oxygen saturation do not exploit the psychological response of humans to associate particular sounds with danger or trouble. Because there is nothing inherent in the pitch of a sound itself which is indicative of a problem, individuals must use high-level thought processes to translate the change of sound pitch into a measure of the patient's condition. Third, various individuals have different abilities to detect differences or changes in sound pitch. Ear defects or injuries of the individual monitoring the patient's condition can impact the individual's ability to immediately detect a problem with the patient's oxygen saturation.

It is an object of the present invention to provide a monitor for a pulse oximeter which emits an audible sound containing information regarding the patient's condition that requires less training and subjective judgment by the individual monitoring the patient's condition.

It is another object of the present invention to provide a monitor for a pulse oximeter which emits an audible sound containing information regarding the patient's condition that can be more quickly interpreted by the individual monitoring the patient's condition.

It is also another object of the present invention to provide a monitor for a pulse oximeter which emits an audible sound containing information regarding the patient's condition that is less affected by hearing disabilities of the individual monitoring the patient's condition.

One aspect of the present invention is a monitor for a pulse oximeter for use in measuring a patient's pulse rate and oxygen saturation level. The monitor comprises a generator which generates an audio signal. The audio signal contains information regarding the patient's pulse rate and oxygen saturation level. A transducer is coupled to the generator to receive the audio signal and to convert the audio signal into audible sounds containing information regarding the patient's pulse rate and oxygen saturation level. Unlike the prior devices, the information is not contained in variations of the pitch of the audible sounds.

Another aspect of the present invention is a monitor for a pulse oximeter for use in measuring a patient's pulse rate and oxygen saturation level. The monitor comprises a generator which generates an audio signal which varies in response to the patient's pulse rate and oxygen saturation level. A transducer is coupled to the generator to receive the audio signal. The transducer converts the audio signal into audible sounds having a volume responsive to the patient's pulse rate and oxygen saturation level.

Another aspect of the present invention is a monitor for a pulse oximeter for use in measuring a patient's pulse rate and oxygen saturation level. The monitor comprises a generator which generates an audio signal which varies in response to the patient's pulse rate and oxygen saturation level. A transducer is coupled to the generator to receive the audio signal. The transducer converts the audio signal into audible sounds with pitches of constant frequency. The audible sounds are responsive to the patient's pulse rate and oxygen saturation level.

BRIEF DESCRIPTION OF THE DRAWINGS

The present application is described below in connection with the attached drawing figures in which:

FIGS. 6a and 6b schematically illustrate similar signals from the heartbeat algorithm and saturation algorithm as illustrated in FIGS. 4a and 4b; and FIG. 6c schematically illustrates the temporal pattern and volume of the audio signal corresponding to the heartbeat and oxygen saturation level of FIGS. 6a and 6b produced by the generator of another preferred embodiment of the present invention.

DETAILED DESCRIPTION OF THE PREFERRED EMBODIMENT

Figure 1:
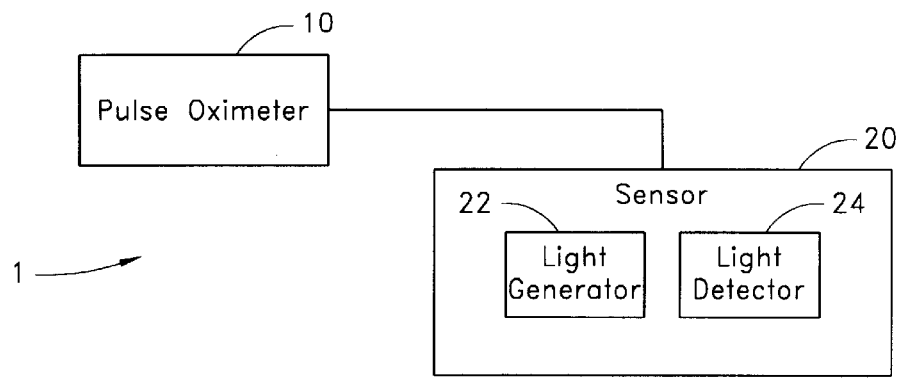
FIG. 1 schematically illustrates a pulse oximetry system utilizing one preferred embodiment of the present invention.

FIG. 1 schematically illustrates a pulse oximetry system 1 utilizing one preferred embodiment of the present invention. The pulse oximetry system 1 comprises a pulse oximeter 10 connected to a sensor 20. The sensor 20 provides to the pulse oximeter 10 a signal indicative of the transmitted light intensity through a section of the body tissue of the patient. The sensor 20 includes a light generator 22 that generates the light incident on the section of body tissue and a light detector 24 that detects the light transmitted through the section of body tissue. Such sensors in view of the disclosures herein are well-known to those skilled in the relevant art.

Figure 2:
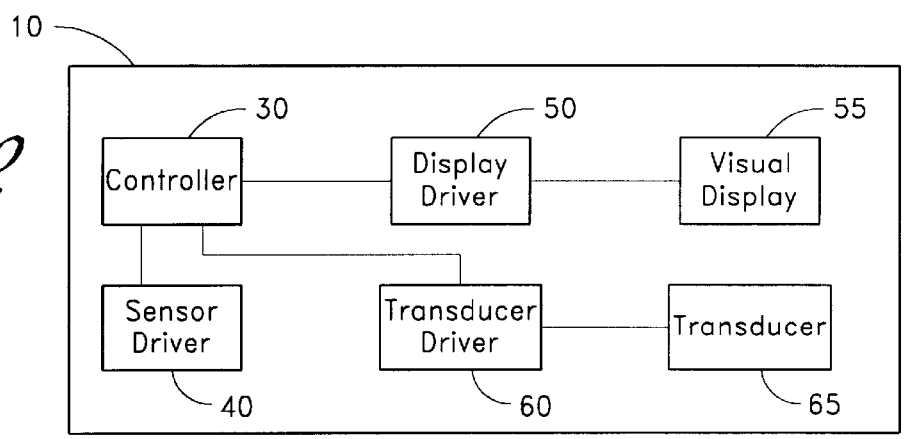
FIG. 2 illustrates a block diagram of the pulse oximeter of FIG. 1.

In FIG. 2, the pulse oximeter 10 comprises a controller 30 which is in communication with a sensor driver 40, a display driver 50 coupled to a visual display 55, and a transducer driver 60 coupled to a transducer (e.g., a speaker) 65. The sensor driver 40 provides the sensor 20 with the power and signals required to operate the light generator 22 and the light detector 24 of the sensor 20, based on the controlling signals from the controller 30. The sensor driver 40 can also advantageously include a signal amplifier to amplify the signals from the sensor 20 to levels which are usable by the controller 30. Upon analysis of the signals from the sensor driver 40, the controller 30 generates signals sent to the display driver 50 and the transducer driver 60. The visual display 55 and transducer 65 are driven by their respective drivers to produce visual and audible signals indicative of the patient's condition. Persons skilled in the art are aware of adequate display drivers, displays, transducer drivers, and transducers to utilize in view of the disclosures herein.

Figure 3:
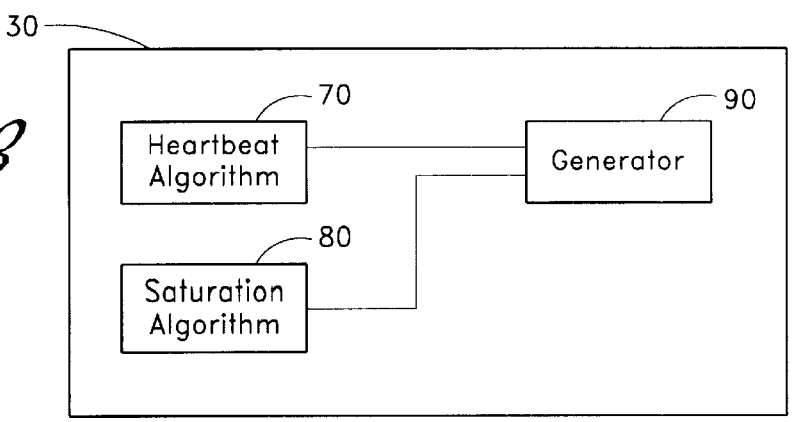
FIG. 3 illustrates a block diagram of particular elements of the pulse oximeter controller of FIG. 2.

FIG. 3 schematically illustrates particular elements of the controller 30 which comprises in part a heartbeat algorithm 70, a saturation algorithm 80, and a generator 90. The heartbeat algorithm 70 and the saturation algorithm 80 are preferably embodied in a microprocessor (not shown) programmed to function as described below. Based on signals from the sensor driver 40 corresponding to the heartbeat of the patient, the heartbeat algorithm 70 generates an output signal which is communicated to the generator 90. The saturation algorithm 80 generates an output signal based on signals from the sensor driver 40 corresponding to the patient's oxygen saturation level. This output signal from the saturation algorithm 80 is then communicated to the generator 90. As it receives the output signals from the heartbeat algorithm 70 and the saturation algorithm 80, the generator 90 generates an audio signal which contains information concerning both the heartbeat and the oxygen saturation level of the patient. The audio signal from the generator 90 is a function of a comparison between the computed oxygen saturation level and various preset levels. This audio signal is then communicated to the transducer driver 60 to be converted by the transducer 65 into sounds audible to the monitoring individual.

Figures 4A, 4B, 4C:
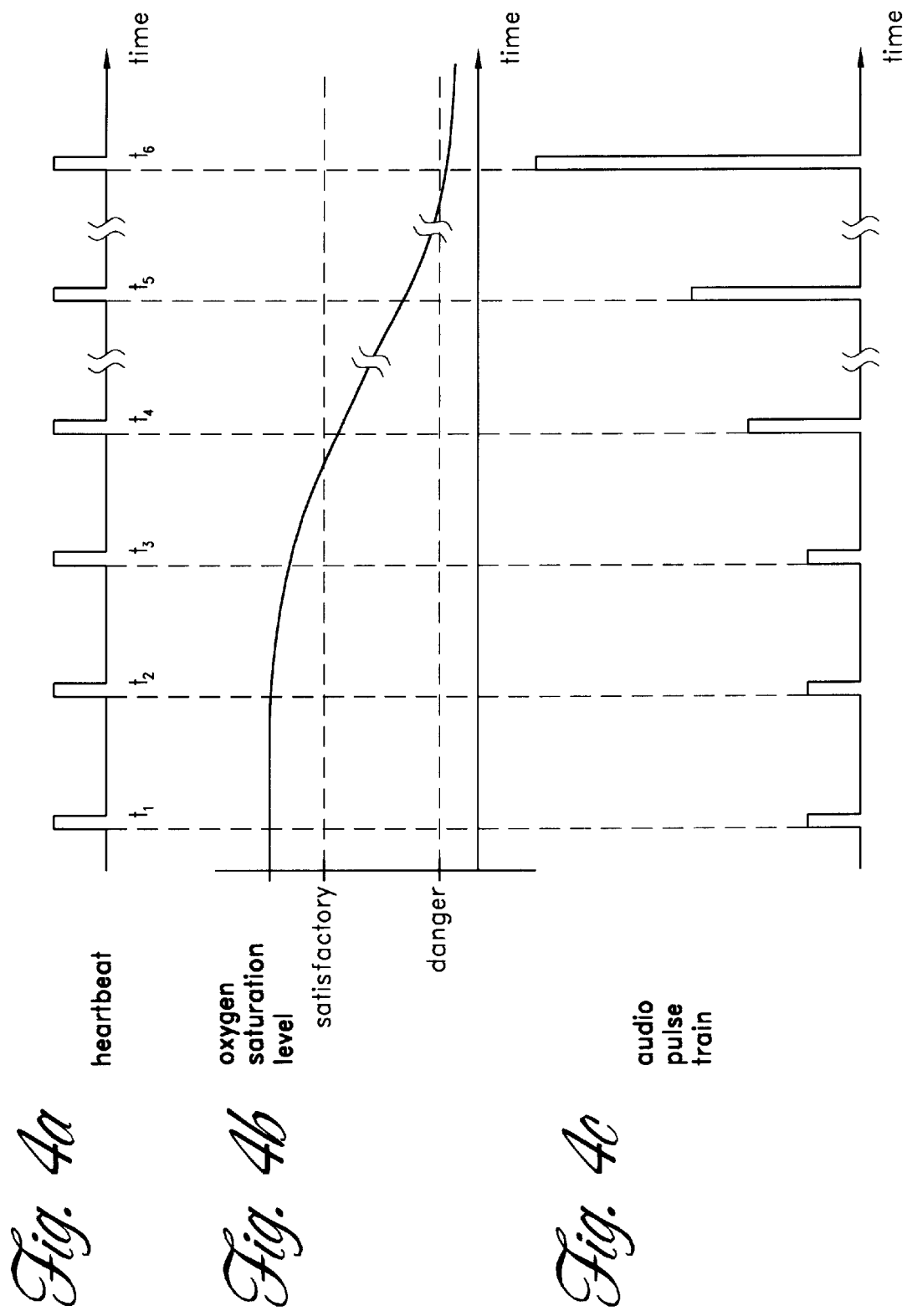
FIG. 4a schematically illustrates the signal produced by the heartbeat algorithm corresponding to a patient's heartbeats.
FIG. 4b schematically illustrates the signal produced by the saturation algorithm corresponding to a patient's oxygen saturation level.
FIG. 4c schematically illustrates the temporal pattern and volume of the audio signal corresponding to the heartbeat and oxygen saturation level of FIGS. 4a and 4b produced by the generator of one preferred embodiment of the present invention.

FIG. 4a illustrates one preferred embodiment of the output signals from the heartbeat algorithm 70 and FIG. 4b illustrates one preferred embodiment of the output signals from the saturation algorithm 80. As shown in FIG. 4a, the heartbeat algorithm 70 produces for each detected heartbeat a corresponding signal which is communicated to the generator 90. Thus, heartbeats detected at times $t_1$, $t_2$, $t_3$, etc., correspond to signal pulses from the heartbeat algorithm 70 at times $t_1$, $t_2$, $t_3$, etc. As shown in FIG. 4b, the saturation algorithm 80 produces a signal corresponding to the patient's oxygen saturation level, which is communicated to the generator 90. In the embodiment shown in FIG. 4b, the patient's oxygen saturation level has decreased below a preset satisfactory level sometime between $t_3$ and $t_4$, dipping below a preset danger level sometime between $t_5$ and $t_6$. Persons skilled in the art recognize that there is a wide variety of possible signals produced by the heartbeat algorithm 70 and signals from the saturation algorithm 80 which can adequately convey information regarding the patient's heartbeat and oxygen saturation level to the generator 90.

Monitors accompanying such pulse oximeters have been disclosed in the prior art. For example, New et al., U.S. Pat. No. 4,653,498 discloses a display monitor which emits an audible sound pulsed in synchroneity with the heartbeat of the monitored patient, with the pitch of the audible sound varying continuously with changes in the oxygen saturation.

FIG. 4c illustrates one preferred embodiment of the resulting audio signal produced by the generator 90. In this preferred embodiment, the audio signal produced by the generator 90 is an audio pulse train, wherein each pulse in FIG. 4c represents a plurality of cycles of an audio tone having a selected duration (e.g., approximately 50 cycles of a 500 Hz tone having a duration of approximately 100 milliseconds). For each heartbeat of the patient, if the patient's oxygen saturation level is above the preset satisfactory level, the generator 90 produces an audio pulse corresponding to an audible sound of a preset volume. However, if the patient's oxygen saturation level has decreased below the preset satisfactory level, the audio pulse from the generator 90 corresponds to louder sounds generated by the transducer 65. The magnitude of the sound volume is a function of the patient's oxygen saturation level as compared to the preset satisfactory level. Additional preset levels may be utilized to produce more significant increases of the sound volume for further reductions of the patient's oxygen saturation level. As in FIG. 4c, if the patient's oxygen saturation level dips below the preset danger level, the audio pulses from the generator 90 correspond to significantly louder sounds generated by the transducer 65. The net effect of this preferred embodiment is to yield audible sounds, in synchroneity with the patient's heartbeat, which become louder as the patient's oxygen saturation level decreases.

Such audible sounds for which the volume is correlated with the patient's oxygen saturation level provide additional benefits not found in the pulse oximeter monitors described in the prior art. First, interpretation of an increasingly louder sound requires less high-level thought processes since it is a less subjective judgment than is the relative pitch of a tone. By judiciously setting the preset oxygen saturation levels and the corresponding sound volumes, the pulse oximeter can be configured to produce unambiguous audible sounds indicative of a patient's oxygen saturation level. Second, individuals monitoring the patient's condition are more psychologically prone to react to increases of sound volume as indications of the patient's deteriorating condition than they are to changes of pitch. Therefore, it is expected that reaction times and urgency will be better correlated with the severity of the patient's condition once the pulse oximeter is properly configured. Third, by utilizing the sound volume as an indication of the patient's oxygen saturation level, the influence of the monitoring individual's hearing ability is lessened, as compared to the prior art systems which utilize pitch to indicate oxygen saturation levels. While the audible sounds in both types of systems must be loud enough for the monitoring individual to hear, the present invention is not vulnerable to any hearing deficiencies of the monitoring individual with respect to pitch. If a sound corresponding to a satisfactory oxygen saturation level is sufficiently loud to be heard, it is probable that the monitoring individual can readily hear increases of the sound's volume associated with reductions of the patient's oxygen saturation level.

Figure 5A:
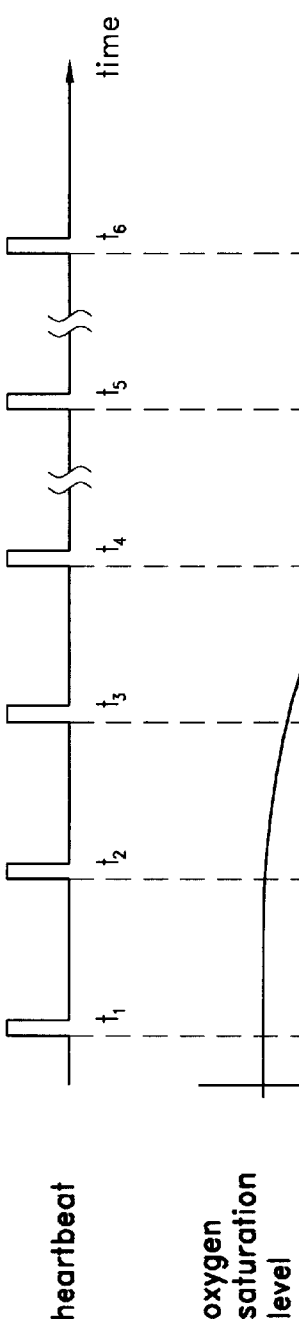
FIGS. 5a and 5b schematically illustrate similar signals from the heartbeat algorithm and saturation algorithm as illustrated in FIGS. 4a and 4b.
Figure 5B:
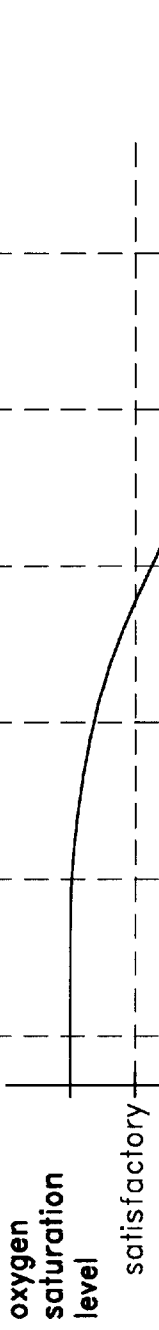
Figure 5C:
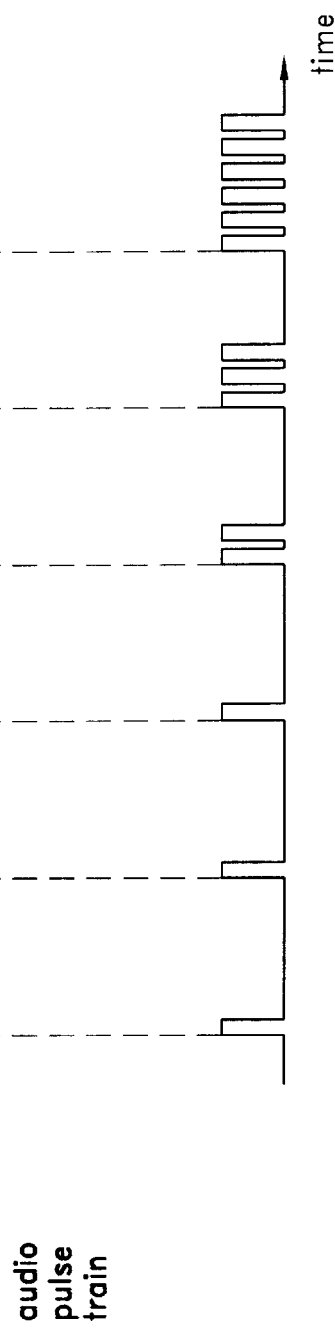
FIG. 5c schematically illustrates the temporal pattern and volume of the audio signal corresponding to the heartbeat and oxygen saturation level of FIGS. 5a and 5b produced by the generator of another preferred embodiment of the present invention.

FIGS. 5a and 5b illustrate similar output signals from the heartbeat algorithm 70 and the saturation algorithm 80 as illustrated in FIGS. 4a and 4b and described above. FIG. 5c illustrates another preferred embodiment of the audio signal produced by the generator 90. In this preferred embodiment, the audio signal produced by the generator 90 is an audio pulse train. For each heartbeat of the patient, if the patient's oxygen saturation level is above the preset satisfactory level, the generator 90 produces a single audio pulse corresponding to a single audible sound of a preset volume. However, if the patient's oxygen saturation level has decreased below the preset satisfactory level, the audio signal from the generator 90 causes additional sounds to be generated by the transducer 65. As in the embodiment illustrated in FIG. 5c, once the patient's oxygen saturation level dips below the preset satisfactory level, the generator 90 produces two or more audio pulses per heartbeat instead of the single audio pulse per heartbeat indicative of satisfactory oxygen saturation levels. Each audio pulse is then communicated to the transducer 65, resulting in two or more audible sounds in rapid succession. The number of audio pulses per heartbeat is a function of the magnitude of the patient's oxygen saturation level as compared to the preset satisfactory level. Additional preset levels may be utilized to produce more numerous audio pulses for further reductions of the patient's oxygen saturation level. As in FIG. 5c, if the patient's oxygen saturation level dips below the additional preset danger level, the generator 90 produces six audio pulses per heartbeat which are communicated to the transducer 65. The net effect of this preferred embodiment is to yield sets of audible sounds in synchroneity with the patient's heartbeat, with the number of sounds in each set becoming larger as the patient's oxygen saturation level decreases.

In FIG. 5c, the audible signal is illustrated as having zero volume between heartbeats and between each pulse in a set of pulses and having maximum volume for each pulse. It should be understood that the volume between heartbeats and between the pulses can be non-zero. Thus, it should be understood that the embodiment of FIG. 5c also illustrates the control of the volume of the audible signal in response to the patient's oxygen saturation level.

Such audible sounds for which the number of sounds per heartbeat is correlated with the patient's oxygen saturation level provide additional benefits not found in the pulse oximeter monitors described in the prior art or in the embodiment illustrated in FIG. 4c. First, interpretation of the number of audible sounds per heartbeat is a less subjective judgment than either the interpretation of relative pitches or relative volumes. By judiciously setting the preset oxygen saturation levels and the corresponding number of tones per heartbeat, the pulse oximeter can be configured to produce unambiguous audible sounds indicative of a patient's oxygen saturation level. Second, individuals monitoring the patient's condition are psychologically prone to react to rapidly repeating sounds as an indication of the patient's deteriorating condition. Once the monitoring individual is informed that numerous sounds in rapid succession means that the patient's condition is deteriorating, it is expected that reaction times and urgency will be better correlated with the severity of the patient's condition once the pulse oximeter is properly configured. Third, by utilizing the number of sounds per heartbeat as an indication of the patient's oxygen saturation level, the influence of the monitoring individual's hearing ability is practically eliminated. As long as the single sound per heartbeat for satisfactory oxygen saturation levels is audible, it is assured that the additional sounds associated with less than satisfactory levels will also be audible.

FIGS. 6a and 6b illustrate similar output signals from the heartbeat algorithm 70 and the saturation algorithm 80 as illustrated in FIGS. 4a and 4b and described above. FIG. 6c illustrates another preferred embodiment of the audio signal produced by the generator 90. In this preferred embodiment, the audio signal produced by the generator 90 is an audio pulse train comprising pulses which have a volume defined by an envelope. The envelope has a shape which varies in response to changes in the patient's oxygen saturation. For each heartbeat of the patient, if the patient's oxygen saturation level is above the preset satisfactory level, the generator 90 produces an audio pulse corresponding to an audible sound with a preset volume shape. As used herein, the term volume shape means the shape of the volume envelope of the audible sound at each moment from the start of one heartbeat to the start of the subsequent heartbeat. In the preferred embodiment illustrated in FIG. 6c, this audible sound has a preset square volume shape (i.e., a single volume level during a time interval). However, if the patient's oxygen saturation level has decreased below the preset satisfactory level, the audio pulses from the generator 90 correspond to audible sounds with different volume shapes. As in the embodiment illustrated in FIG. 6c, once the patient's oxygen saturation level dips below the preset satisfactory level, the audio pulses communicated to the transducer 65 result in audible sounds with stepped volume shapes (i.e., multiple volume levels during a time interval) with two volume levels. The volume shape of each audible sound is a function of the magnitude of the patient's oxygen saturation level as compared to the preset satisfactory level. Additional preset levels may be utilized to produce audible sounds with other volume shapes for further reductions of the patient's oxygen saturation level. As in FIG. 6c, if the patient's oxygen saturation level dips below the additional preset danger level, the audio pulses from the generator 90 result in audible sounds with a stepped volume shape with three volume levels. Persons skilled in the art recognize that a wide variety of volume shapes (e.g., square, stepped, triangular, sinusoidal) can be utilized when practicing the present invention. The net effect of this preferred embodiment is to yield sets of audible sounds in synchroneity with the patient's heartbeat, with the volume shape of the sounds in each set varying as the patient's oxygen saturation level decreases.

For some persons, the variations of the volume shape of the audible sound per heartbeat may be more recognizable than either the differing volumes among audible sounds corresponding to different heartbeats or the number of sounds per heartbeat. In particularly preferred embodiments, the embodiment to be used at any given time may be selected by the setting of an output mode selector (e.g., a switch, knob, or program) of the pulse oximeter.

This invention may be embodied in other specific forms without departing from the essential characteristics as described herein. The embodiments described above are to be considered in all respects as illustrative only and not restrictive in any manner. The scope of the invention is indicated by the following claims rather than by the foregoing description. Any and all changes which come within the meaning and range of equivalency of the claims are to be considered within their scope.

What is claimed is:

1. A monitor for a pulse oximeter for use in measuring a patient's pulse rate and oxygen saturation level, comprising:
    a generator which generates an audio signal, wherein the audio signal contains information regarding the patient's pulse rate and oxygen saturation level; and
    a transducer coupled to the generator to receive the audio signal and to convert the audio signal into audible sounds containing information regarding the patient's pulse rate and oxygen saturation level, wherein the information is not contained in variations of the pitch of the audible sounds.

2. The monitor as defined in claim 1, wherein the information regarding the patient's pulse rate is expressed by sets of audible sounds pulsed in synchroneity with the heartbeat of the patient.

3. The monitor as defined in claim 2, wherein the sets of audible sounds each contain one or more audible sounds.

4. The monitor as defined in claim 2, wherein the information regarding the patient's oxygen saturation level is expressed by variations of the volume of the audible sounds with the patient's oxygen saturation level.

5. The monitor as defined in claim 4, wherein the volume of the audible sounds increases as the patient's oxygen saturation level decreases.

6. The monitor as defined in claim 5, wherein the magnitude of the audible sound volume is a function of the patient's oxygen saturation level as compared to a set of preset levels.

7. The monitor as defined in claim 2, wherein the information regarding the patient's oxygen saturation level is expressed by variations of the number of audible sounds in each set of audible sounds with the patient's oxygen saturation level.

8. The monitor as defined in claim 2, wherein the number of audible sounds in each set of audible tones increases as the patient's oxygen saturation level decreases.

9. The monitor as defined in claim 8, wherein the number of audible sounds in each set of audible sounds is a function of the patient's oxygen saturation level as compared to a set of preset levels.

10. The monitor as defined in claim 2, wherein the information regarding the patient's oxygen saturation level is expressed by variations of the volume shape of the audible sounds in each set of audible sounds with the patient's oxygen saturation level.

11. The monitor as defined in claim 10, wherein the volume shape of the audible sounds in each set of audible sounds is a function of the patient's oxygen saturation level as compared to a set of preset levels.

12. The monitor as defined in claim 1, wherein the transducer is a speaker.

13. A monitor for a pulse oximeter for use in measuring a patient's pulse rate and oxygen saturation level, comprising:
    a generator which generates an audio signal which varies in response to the patient's pulse rate and oxygen saturation level; and
    a transducer coupled to the generator to receive the audio signal, said transducer converting the audio signal into audible sounds having a volume responsive to the patient's pulse rate and oxygen saturation level.

14. The monitor as defined in claim 13, wherein the volume of the audible sounds varies in response to changes in the oxygen saturation.

15. The monitor as defined in claim 13, wherein the volume of the audible sounds changes from a minimum value to a maximum value in the form of at least one pulse per heartbeat, and wherein the number of pulses per heartbeat varies in response to changes in the oxygen saturation.

16. The monitor as defined in claim 13, wherein the volume of the audible sounds has an envelope that varies in shape in response to changes in the oxygen saturation.

17. A monitor for a pulse oximeter for use in measuring a patient's pulse rate and oxygen saturation level, comprising:
    a generator which generates an audio signal which varies in response to the patient's pulse rate and oxygen saturation level; and
    a transducer coupled to the generator to receive the audio signal, said transducer converting the audio signal into audible sounds with pitches of constant frequency, and which are responsive to the patient's pulse rate and oxygen saturation level.

* * * * *